US005741283A

United States Patent [19]
Fahy

[11] Patent Number: 5,741,283
[45] Date of Patent: Apr. 21, 1998

[54] VESSEL AND DUCT SALVAGE DEVICE AND METHOD

[75] Inventor: Gregory M. Fahy, Gaithersburg, Md.

[73] Assignees: LRT, Inc.; Organ, Inc., both of Chicago, Ill.

[21] Appl. No.: 778,746

[22] Filed: Jan. 6, 1997

Related U.S. Application Data

[63] Continuation of Ser. No. 409,706, Mar. 24, 1995, abandoned.

[51] Int. Cl.⁶ ................................................. A61B 17/00
[52] U.S. Cl. ............................ 606/157; 606/151; 606/213; 227/902
[58] Field of Search ............................ 606/151, 157, 606/158, 219, 221, 213, 215, 216; 227/902

[56] References Cited

U.S. PATENT DOCUMENTS

| | | | |
|---|---|---|---|
| 3,339,247 | 9/1967 | Geisinger | 606/151 |
| 3,570,497 | 3/1971 | Lemole | 606/151 |
| 3,577,601 | 5/1971 | Mariani | 606/151 |
| 4,950,285 | 8/1990 | Wilk | 606/151 |
| 5,211,649 | 5/1993 | Kohler et al. | 606/139 |
| 5,383,882 | 1/1995 | Buess et al. | 606/151 |

*Primary Examiner*—Jeffrey A. Schmidt
*Attorney, Agent, or Firm*—Oliff & Berridge, PLC

[57] ABSTRACT

A vessel or biological duct repair device and method includes a strap of material that is placed around the exterior surface of the vessel and drawn snugly about the vessel. The device can be used to seal an incision or rupture in a vessel, to correct an aneurysm, or to apply pressure to the exterior of the vessel. The device may also include a projection or other means to aid grasping and positioning the device. The device may include a closure mechanism that allows the device to assume various internal diameters or to exert varying amounts of pressure to a vessel. A layer of procoagulant material may be provided on a vessel contacting surface of the device to promote clotting of any blood that escapes the vessel. The device may be prevented from moving relative to a surrounded vessel by ridges provided on the vessel contacting surfaces, by suturing the device to surrounding tissue, or by applying an adhesive to fix the device to the vessel.

23 Claims, 9 Drawing Sheets

FIG. 1A
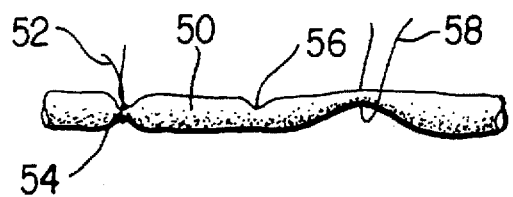
FIG. 1B
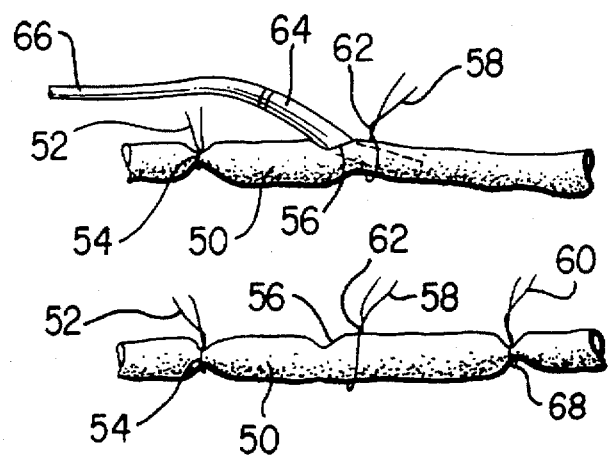
FIG. 1C
FIG. 1D
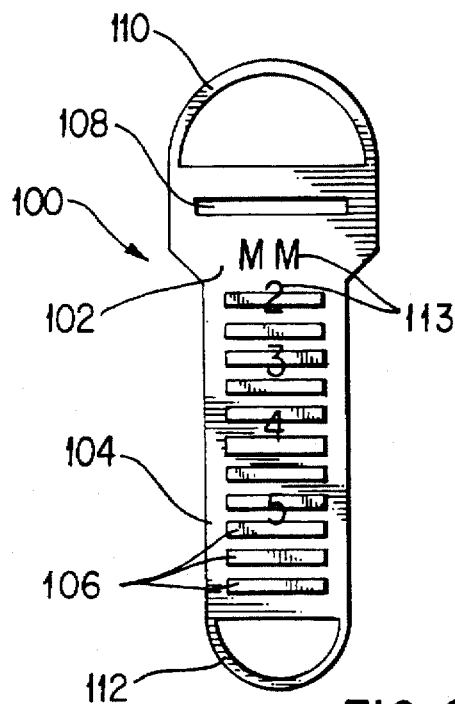
FIG. 2
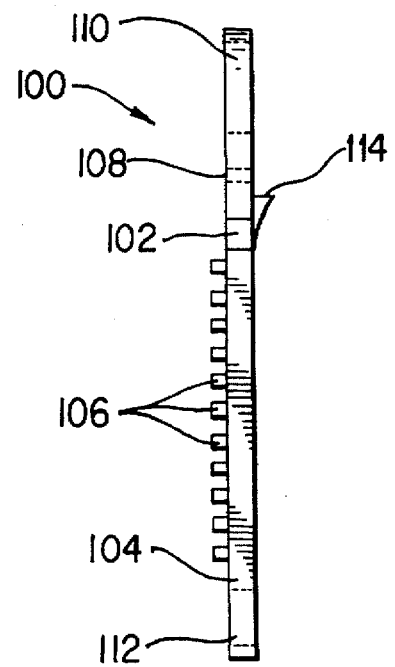
FIG. 3

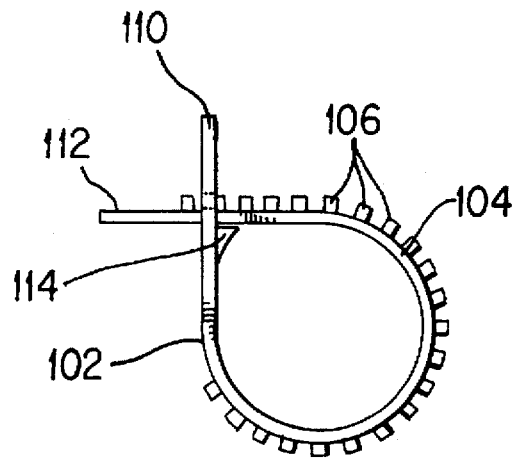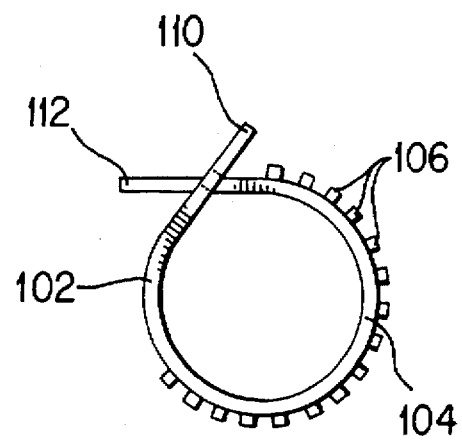
FIG. 4A  FIG. 4B
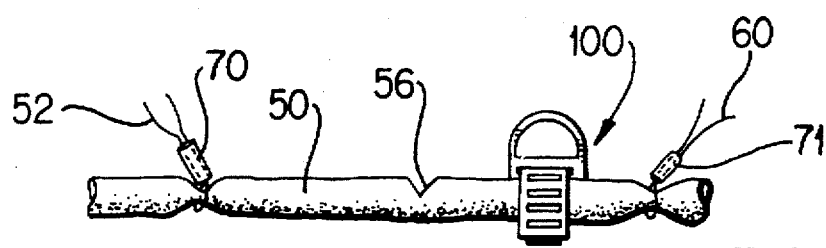
FIG. 5A
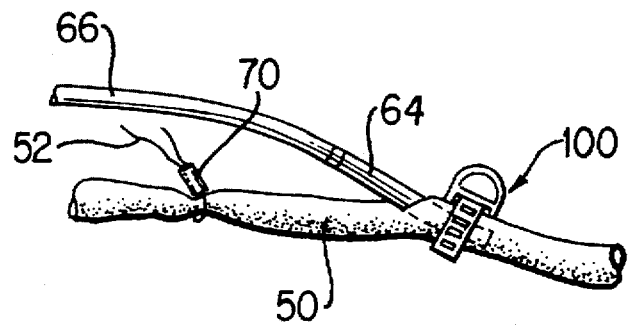
FIG. 5B
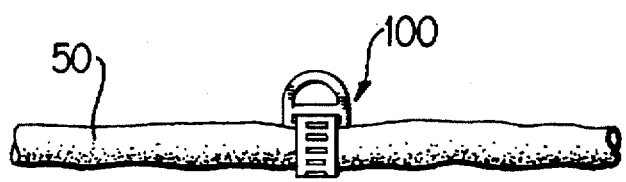
FIG. 5C

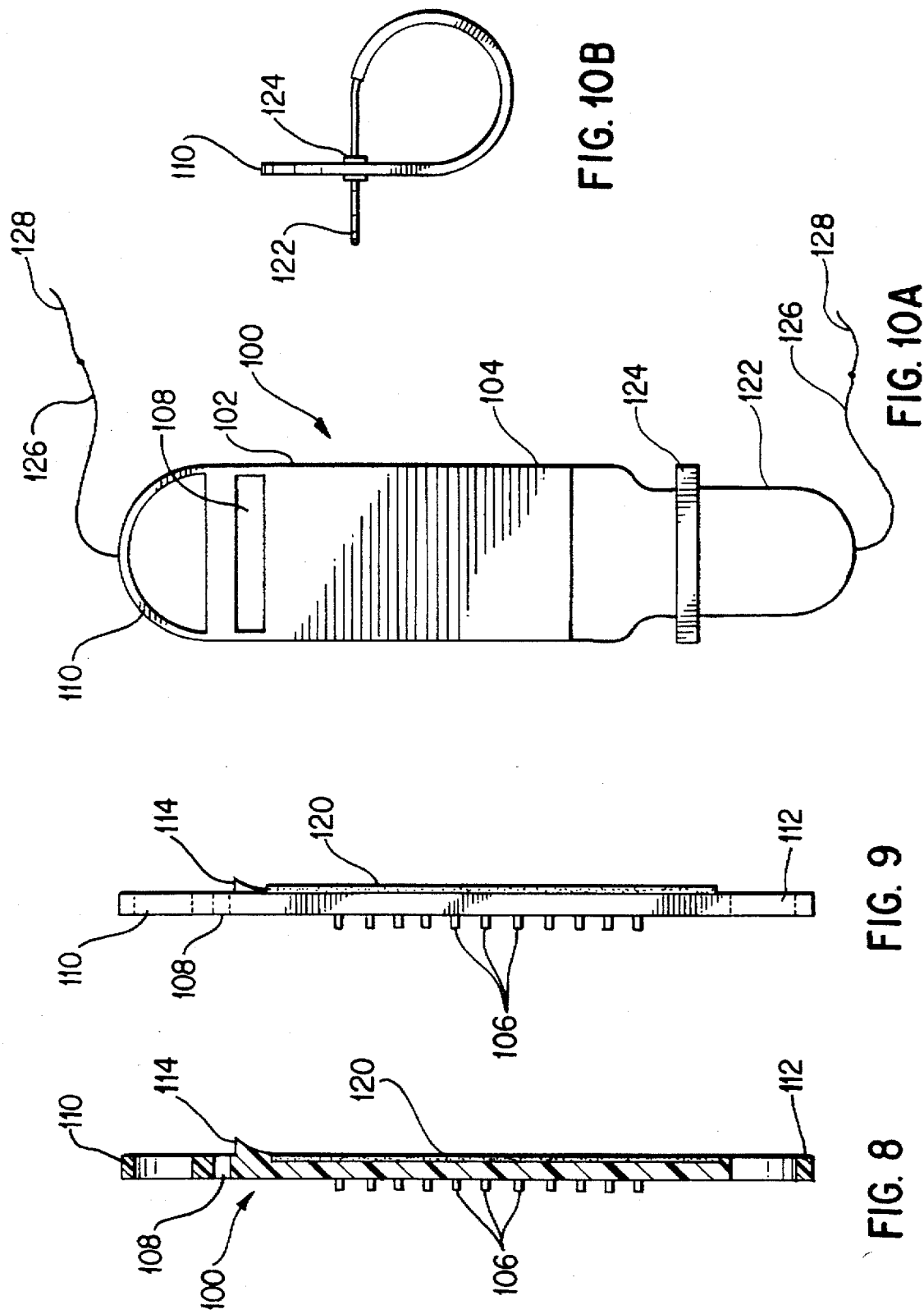

5,741,283

VESSEL AND DUCT SALVAGE DEVICE AND METHOD

This is a continuation of application Ser. No. 08/409,706 filed Mar. 24, 1995 now abandoned.

BACKGROUND OF THE INVENTION

The invention relates to vascular surgery, and in particular to devices and methods for sealing vascular or biological duct breaches, for correcting vascular aneurysms, and for applying pressure to the exterior of a vessel or biological duct.

Vascular surgery is fundamental to surgery and much of experimental biology. Cannulating vessels, vascular perfusion, the repair of traumatic or accidental vascular breaches and the repair of aneurysms are all common medical procedures requiring vascular surgery.

Current vascular surgical techniques may require permanent ligation of a section of a blood vessel. For example, many animal physiology laboratories measure blood pressure invasively through the introduction of a cannula into a major vessel such as the femoral artery. In addition, such laboratories may carry out studies of cardiopulmonary bypass in which both a femoral artery and a femoral vein are cannulated to institute a bypass.

Medical research laboratories often lack the expertise and the time required to surgically repair the incisions made to these vessels during cannulation. As a result, they permanently ligate the vessels at the end of the experiment, thereby permanently blocking blood flow through the vessel. The blockage of blood flow can cause permanent damage to the limb or the surrounding regions which are normally supplied by the ligated vessel, as well as post-operative tenderness in the affected area.

The basic procedure for cannulating a vessel is shown in FIGS. 1A–1D. FIG. 1A shows a vessel 50 prior to cannulation.

FIG. 1B shows the beginning steps of the procedure, wherein a first ligature 52 and a second ligature 58 are placed around first and second ends, respectively, of the vessel 50. The first ligature 52 is tied off in a knot 54 to prevent blood flow through the vessel 50. The second ligature 58 is pulled tight to prevent blood flow through the vessel 50, and an incision 56 is made in the middle of the vessel to allow insertion of a cannula.

As shown in FIG. 1C, a cannula 64 is then inserted into the incision 56. The second ligature 58 is tightened and tied around the vessel (this arrangement is commonly called a circular suture) to draw the vessel tightly around the exterior of the cannula 64 to prevent leakage of blood, and to prevent the cannula 64 from coming out of the vessel 50. The circular suture often damages the vascular endothelium due to the high pressure applied to the lining of the vessel at the site of the circular suture. The tube 66 may lead to a blood pressure monitoring device, or some other monitoring instrument.

As shown in FIG. 1D, when the cannula is no longer needed, a third ligature 60 is tied around the vessel 50 to cut off blood flow through the vessel 50. The cannula 64 is then pulled out of the vessel, with or without first cutting the second ligature 58. The two tied ligatures 52 and 60 permanently prevent blood flow through the vessel 50 so that blood will not escape the incision 56.

The permanent blockage of blood flow can result in the above mentioned problems. In addition, the ligatures used during cannulation are necessarily much longer than the circumference of the vessel. The additional length can be awkward during surgery, and may require trimming and excess manipulation, all of which increases the amount of time spent in surgery. In addition, some ligatures require immersion in a liquid prior to handling, thereby increasing the amount of time spent in surgery. Moreover, the ligatures are often difficult to secure because the initial loop placed around the vessel may slip while the second loop, which secures the first loop, is being prepared. Furthermore, available suture material is prone to breakage if excess pressure is applied.

To avoid unnecessary damage to the patient, and unnecessary discomfort after surgery, it is necessary to repair the incision in the vessel made during cannulation so that blood flow through the vessel may be restored. If an attempt is made to suture the incision 56 so that blood flow can be restored through the vessel 50, it may be necessary to resect the area of the vessel surrounding the circular suture because the circular suture may damage the vascular endothelium due to the high pressure applied to the lining at the site of the circular suture. When sutures are used to repair an incision in a vessel, the sutures are subject to loosening, leakage, and clot promotion. In addition, the edges of the incision may break away from the sutures, creating an additional gap in the vessel and causing internal bleeding. Finally, most people who are capable of cutting and cannulating a vessel are not capable of suturing it closed.

A vascular aneurysm occurs when a weak section of a vessel expands outward under the influence of the blood pressure. If the aneurysm ruptures, the resulting internal bleeding can be fatal.

In one prior art method of correcting an aneurysm, the section of the vessel having the aneurysm is removed, and the severed ends of the vessel are attached to one another. In another method, the damaged section of the vessel is removed and replaced with a prosthetic material or a vessel graft. These methods can lead to internal bleeding if the severed ends of the vessel are not perfectly sutured.

Each of these prior art methods also require that blood flow through the vessel be halted until the aneurysm has been corrected. If the aneurysm is formed on a vessel leading to the brain or other critical organs, halting the flow of blood through the vessel can cause critical damage to the patient.

In addition, if a prosthesis is inserted, the prosthesis material must be biologically inert so that blood does not clot on the prosthesis. If a vascular graft is used, it must be an excellent match (which is very unusual) so that the patient's body does not attempt to reject the material. Furthermore, the prosthetic material is subject to deterioration over time, raising the possibility of a failure of the material.

SUMMARY OF THE INVENTION

The invention is a device and method for repairing a vessel or duct by placing a repair device around the vessel to seal an incision or break in the vessel. A device embodying the present invention could also be used to apply a desired amount of pressure to the exterior of a vessel to safely collapse an aneurysm, or as a less damaging alternative to a circular suture.

A device embodying the invention may include a strap designed to surround a vessel, and a closure device that allows the strap to be adjusted to close at various diameters, and with varying amounts of tension. The device may be made of a material that can be left in place indefinitely, or it may be made of a resorbable material which dissolves over time. The length, width and thickness can vary depending upon the application. The device may also be provided with means for securing the device to nearby tissues to prevent the device from moving relative to the repaired vessel.

Although the device is primarily intended for use on blood vessels, the device could also be used on biological ducts such as a bile duct, a thoracic duct, a pancreatic duct, an intestinal segment, a trachea or an esophagus.

BRIEF DESCRIPTION OF THE DRAWINGS

Embodiments of the invention will be described with reference to the following drawing figures, wherein like elements are identified with like reference numerals, and wherein:

FIGS. 1A–1D illustrate a cannulation procedure;

FIG. 2 is a plan view of a device embodying the invention in an open position;

FIG. 3 is a side view of a device embodying the invention in an open position;

FIGS. 4A and 4B are side views of devices embodying the invention in closed positions;

FIGS. 5A–5C illustrate a cannulation procedure using a device embodying the present invention;

FIG. 8 is a sectional side view of a device embodying the present invention;

FIG. 9 is a side view of a device embodying the present invention;

FIGS. 10A and 10B are plan and side views, respectively, of a device embodying the present invention in open and closed positions, respectively;

DETAILED DESCRIPTION OF PREFERRED EMBODIMENTS

Figure 6A:
FIG. 6A–6C illustrate development of a vascular aneurysm.

The embodiments of the invention described herein could be used to repair blood vessels, or any type of biological duct such as a bile duct, a thoracic duct, a pancreatic duct, an intestinal segment, a trachea or an esophagus. The term vessel, as used in the specification, abstract and claims, is intended to encompass both blood vessels and any other types of biological ducts.

A vessel repair device 100 embodying the present invention is shown in an open position in FIGS. 2 and 3. The device comprises a thin strip of flexible material having an upper section 102 and a lower section 104. The width of the lower section 104 is smaller than the width of the upper section 102. A plurality of ridges 106 are formed on the front side of the vessel repair device 100. A long thin aperture 108 is formed through the upper section 102. An upper strap 110 may be attached to the upper section 102, and a lower strap 112 may be attached to the lower section 104. The upper and lower straps 110, 112 may be integrally formed with the material comprising the upper and lower sections 102, 104, or the upper and lower straps 110, 112 may be formed of separate pieces of material that are joined to the upper and lower sections 102, 104. Characters may be printed on the front face of the device 100 to indicate the diameter of the device when it is in a closed position. A triangular shaped projection 114 may be formed on the rear surface of the device.

Side views of devices embodying the invention in closed positions are shown in FIGS. 4A and 4B. The lower strap 112 and the lower section 104 have been bent around and inserted through the aperture 108 in the upper section 102. The sections of the strap having ridges 106 are thicker than the height of the aperture 108. Once the lower section 104 has been passed far enough through the aperture 108 so that ridges 106 are located on each side of the upper section 102, physical interference between the ridges 106 and the aperture 108 will prevent the lower section 104 from escaping from the aperture 108.

FIG. 4A illustrates a device wherein the lower section 104 passes through the upper section 102 in a direction substantially perpendicular to the front and rear surfaces of the device. The triangular projection 114 on the rear surface of the device aids in forming a cylindrical shape inside the closed device so that no gaps will exist between the strap and the encircled vessel. This ensures that pressure is evenly applied around the entire circumference of a vessel. The inside diameter of the device can be varied by drawing the lower section 104 through the aperture 108 an appropriate amount.

FIG. 4B illustrates a device wherein the aperture 108 is formed through the material of the upper section 102 at an angle relative to the front and rear surfaces of the device. As a result, the interior of the device forms a more cylindrical shape than the interior of the device shown in FIG. 4A. This reduces or eliminates the need for a triangular projection 114 on the rear surface of the device.

FIGS. 5A–5C illustrate how a device embodying the present invention can be used in a vascular cannulation procedure, and how the device can be used to seal the incision in the vessel resulting from the cannulation procedure. In FIG. 5A a first ligature 52 is used with a snare device 70 to block blood flow through a first end of the vessel 50. A repair device 100 embodying the invention is placed loosely around the vessel 50. A second ligature 60 is used with a second snare device 71 to block blood flow through a second end of the vessel 50. An incision 56 is then made in the vessel 50.

As shown in FIG. 5B, a cannula 64 is then inserted into the incision 56. The vessel repair device 100 is moved along the vessel so that it surrounds the end of the cannula 64, and the device 100 is drawn tightly around the vessel 50 so that no blood can leak from the incision 56. The second ligature is then loosened so that blood can flow into the cannula 64 and through the attached tube 66, or so that pressure in the vessel 50 can be communicated to an external pressure transducer located on the tubing 66. This arrangement could also be used to deliver a fluid to the vessel 50 through the tube 66 and cannula 64.

When the cannula 64 is to be removed, the second ligature 60 and the second snare device 71 are used to again block the flow of blood through the vessel 50. The vessel repair device 100 is loosened, and the cannula 64 is removed from the incision 56. The vessel repair device 100 is then positioned so that it covers the incision 56, and the device is drawn tightly around the vessel to seal off the incision 56. The first and second ligatures 52, 60 and the first and second snare devices 70, 71 are then removed so that blood flow through the vessel can be restored.

The vessel repair device 100 holds the incision 56 closed until the vessel heals itself. A pro-coagulant material may be applied to the interior surface of the device to promote clotting of any blood leaking from the device 100. The device 100 may be made of a resorbable material so that after the vessel has repaired itself, the vessel repair device 100 dissolves away. In addition, the vessel repair device 100 may be prevented from sliding along the longitudinal axis of the vessel by suturing it to surrounding tissue. Alternately, a fibrin glue or some other adhesive, or immobilization means may be used to fix the device to the vessel.

Figure 6B:
Figure 6C:
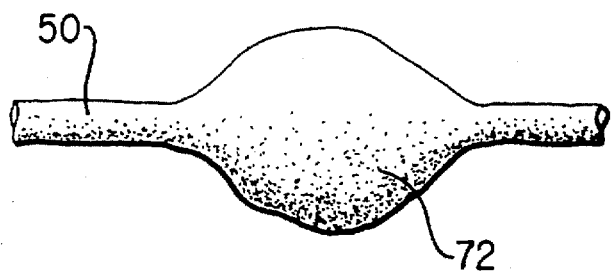

A device embodying the present invention may also be used to correct vascular aneurysms. Vascular aneurysms tend to develop over a period of time. FIGS. 6A–6C show the development of an aneurysm. FIG. 6A shows a vessel 50 in its normal state. FIG. 6B shows an aneurysm 70 beginning to develop in the vessel 50. FIG. 6C shows a fully developed aneurysm 72 in the vessel 50.

Figure 7A:
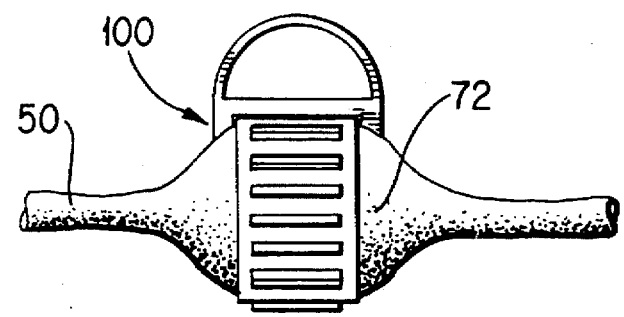
FIGS. 7A–7C illustrate how a device embodying the present invention can be used to correct a vascular aneurysm.
Figure 7B:
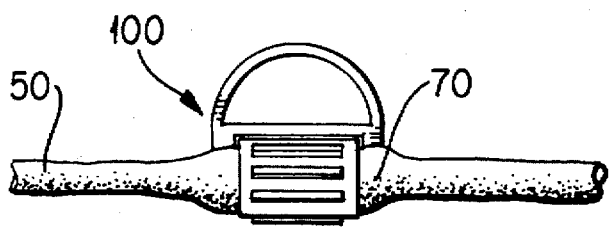
Figure 7C:
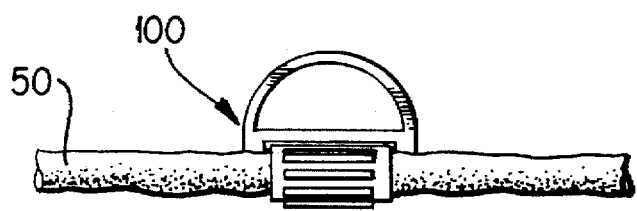

FIGS. 7A–7C illustrate how a device embodying the present invention can be used to correct an aneurysm. As shown in FIG. 7A, a device 100 embodying the present invention is loosely wrapped around the exterior of a fully developed aneurysm 72, and the lower section of the device is inserted through the aperture. The vessel repair device 100 is then gradually tightened around the aneurysm to reduce the diameter of the aneurysm. FIG. 7B shows the vessel repair device 100 tightened around the vessel 50 to reduce the size of the aneurysm 70. FIG. 7C shows a fully tightened vessel repair device 100 which has restored the vessel 50 to its normal size. The device 100 may extend beyond the boundaries of the aneurysm to prevent lateral ruptures of the aneurysm. The device may also have lateral ridges to help prevent lateral ruptures.

The vessel repair device 100 can be formed of a biologically neutral material so that the device 100 permanently remains around the vessel 50 to prevent a reoccurrence of the aneurysm 72. To ensure that the device 100 does not move along the vessel 50 in the longitudinal axial direction, the device 100 can be immobilized by suturing it to surrounding tissue, or by attaching it to the vessel 50 with a fibrin glue or other suitable material.

The repair device could be used with an adhesive sheet that is applied to the aneurysm before the repair device is placed around the aneurysm. The adhesive sheet may be helpful in avoiding rupture of the aneurysm during tightening of the device. In addition, compression may be limited as necessary to avoid rupturing the aneurysm while nevertheless preventing further ballooning of the aneurysm that could lead to a rupture.

Using a vessel repair device embodying the present invention to correct an aneurysm has several advantages over the above described prior art methods of correcting aneurysms. Most importantly, use of the vessel repair device does not require that blood flow through the vessel be temporarily interrupted. In addition, no section of the original vessel need be removed. This virtually eliminates the possibility of internal bleeding and the problems associated with the a prosthesis. This would also allow correction of an aneurysm in instances where surgery to correct an aneurysm is impossible.

FIG. 8 shows a sectional side view of a vessel repair device 100 embodying the present invention. In this embodiment, a layer of pro-coagulant material 120 is formed in a recessed section on the back of the device. The pro-coagulant material could be comprised of any sort of material that promotes the coagulation of blood, such as Avitine flour, fibrin glue, fibrinogen and/or thrombin powder. The pro-coagulant material will ensure that any blood that escapes a vessel despite the application of pressure by the device, will rapidly clot.

FIG. 9 shows a side view of another embodiment of the present invention. In this embodiment, an anti-coagulant material layer 120 is formed on the rear surface of the device. When the device is curled into its closed position, some of the anti-coagulant material layer 120 will be scraped off the rear surface by the triangular projection 114. The scraped off material may help to form a more perfect cylindrical shape in the interior of the device, thus applying more even pressure to the exterior of the vessel.

Another embodiment of the vessel repair device is shown in FIGS. 10A and 10B. In this embodiment, a larger aperture 108 is formed in the body of the device. A thin adjustment tab or loop 122 extends from the lower section 104, and passes through an adjustment bar 124. To apply the device 100 to a vessel, the adjustment tab or loop 122 is passed through the aperture 108, and the adjustment bar 124 is affixed to the interior of the aperture 108, as shown in FIG. 10B.

The adjustment bar 124 tightly grasps the adjustment tab or loop 122, but allows the loop to slide through the adjustment bar 124 to adjust the interior diameter of the device 100. Once the device has been placed around a vessel, the adjustment tab or loop 122 is slowly drawn through the adjustment bar 124 until the appropriate amount of pressure has been applied to the exterior of a vessel. This allows quick easy adjustment of the device around the vessel, and allows the device to assume any of an infinite number of inner diameters.

Ligatures 126 and suture needles 128, may also be attached to the device 100 at various locations. After the device has been secured around a vessel, the needles 128 may be used to suture the device 100 to surrounding tissue to immobilize the device.

Another device embodying the present invention is shown in FIGS. 11A–11D. The device 100 includes a head 131, and a strap 136. The head has a projection 130 to facilitate positioning and manipulation of the device 100. The strap includes a plurality of raised portions 138 that allow the device to assume a plurality of internal diameters, and to apply varying amounts of pressure to the exterior of a vessel. The strap has a pointed end 137, that can be inserted into a channel 134 formed in the head 131. The pointed end 137 of the strap 136 and the tapered ends of the mouth of the channel 134 aid the insertion of the strap into the channel 134. The pointed end 137 can then be drawn out the top of the head 131 to adjust the internal diameter of the device 100. In addition, a tapered end 139 of the underside 133 of the head 131 helps to assure that no gap will be formed between the internal diameter of the device and the exterior of a vessel.

Figure 12:
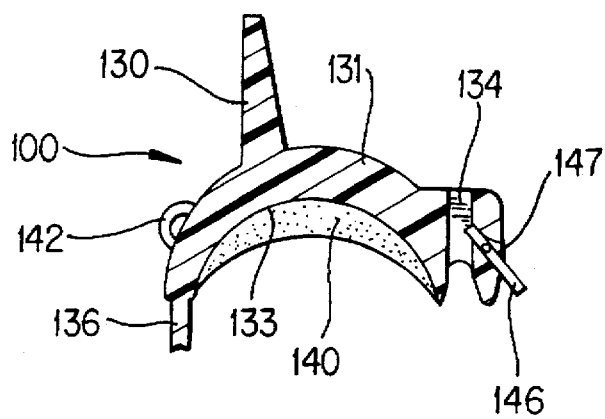
FIG. 12 is a sectional side view of the top portion of a device embodying the present invention.

FIG. 12 shows the head 131 and a portion of a strap 136 of a device embodying the invention. A pro-coagulant material layer 140 is formed on the semicircular underside 133 of the head 131. The pro-coagulant material layer 140 helps to clot any blood that escapes from the vessel after the device 100 has been applied to a vessel. In addition, a tab or loop 142 is provided on the exterior of the head 131 to allow the device to be easily sutured to surrounding tissues to immobilize the device.

The embodiment of the device 100 shown in FIG. 12 also includes a pawl 146, rotatably mounted on a pin 147. The pawl 146 extends into the channel 134. The pawl 146 is designed to interact with recesses (not shown) formed on the surface of a strap 136. When the strap is drawn through the channel 134, the pawl 146 will fall into the recesses on the strap to prevent backward movement of the strap. If it becomes necessary to re-adjust the device, pressing on the protruding portion of the pawl 146 will cause the pawl to rotate about pin 147 and to disengage from the recesses on the strap. The strap could then be loosened and re-set. Once the device is correctly placed around a vessel, the protruding portion of the pawl could be clipped off to prevent accidental release of the device.

Figure 11A:
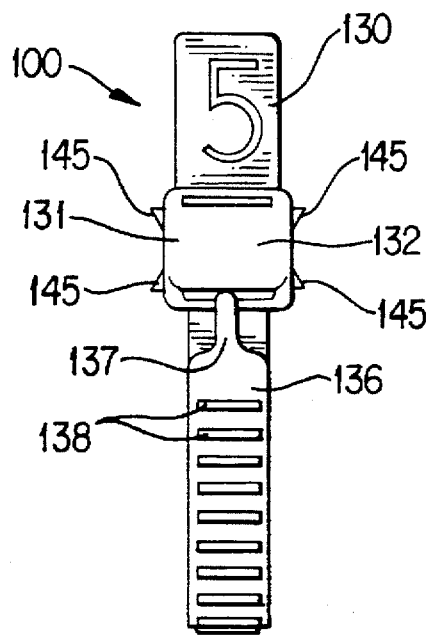
FIGS. 11A–11D are plan, sectional side, sectional side and perspective views, respectively, of a device embodying the present invention.
Figure 11B:
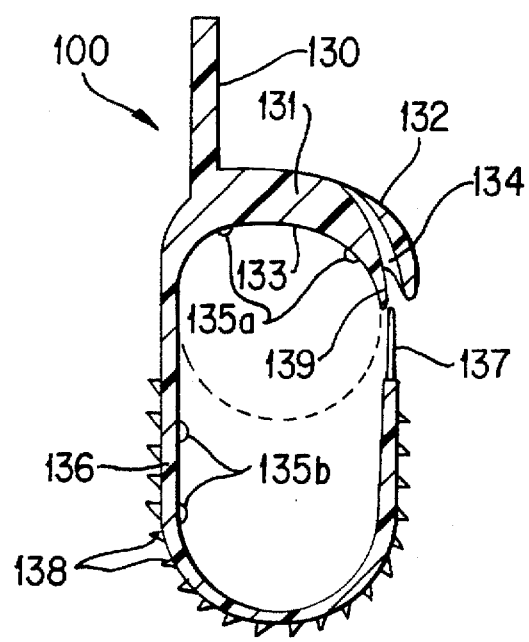
Figure 11C:
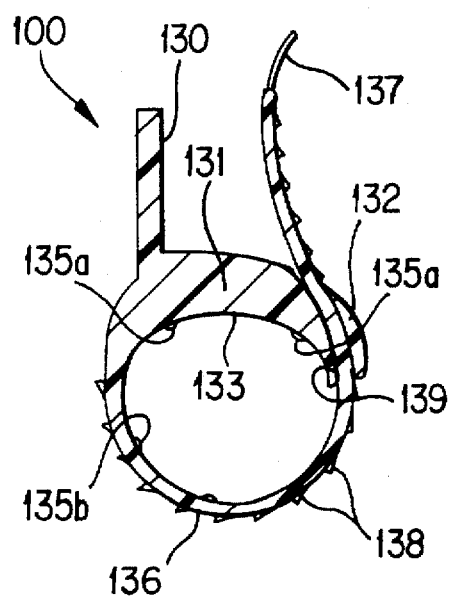
Figure 11D:
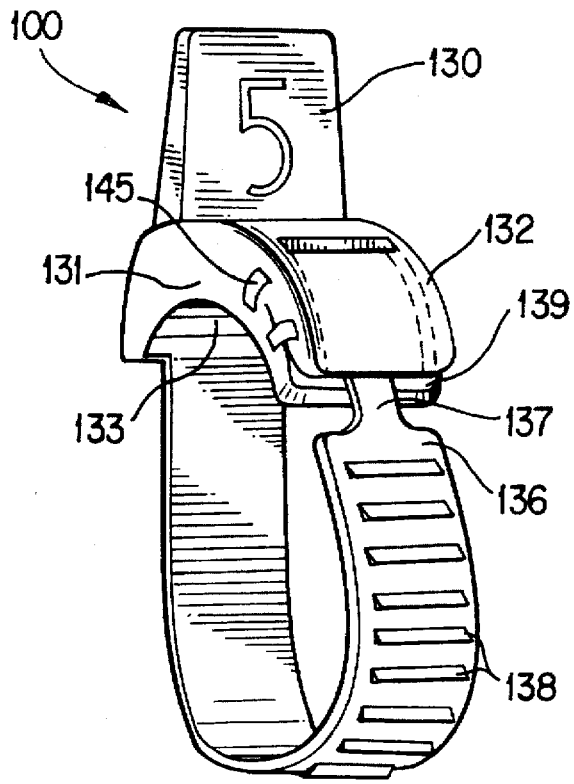

The head 131 of the device 100 shown in FIGS. 11-11D and 12 is ideally made of a transparent material so that a surgeon can see a vessel through the head while the device is being applied to the vessel. The top of the head 131 may be shaped or treated to reduce glare and to improve the visibility of the underlying vessel. Often, incisions in a vessel will not come cleanly closed after removal of a cannula, particularly before blood flow is restored through the vessel. By allowing the surgeon to see the vessel through the top of the head 131, the surgeon can take steps to assure the device is properly positioned, and that the edges of an incision are as close together as possible.

The strap 136 attached to the head 131 is ideally made of an opaque or colored material rather than a transparent material so that the surgeon can easily see the strap through the transparent head, and so that the strap can be easily distinguished from the head 131 and the surrounding tissues. This will also aid the surgeon in inserting the tip 137 of the strap 136 through the channel 134 of the head 131.

Figure 13A:
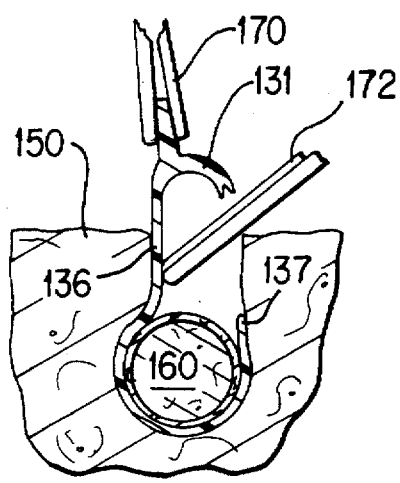
FIGS. 13A–13D illustrate how a device embodying the present invention is attached around a vessel.
Figure 13B:
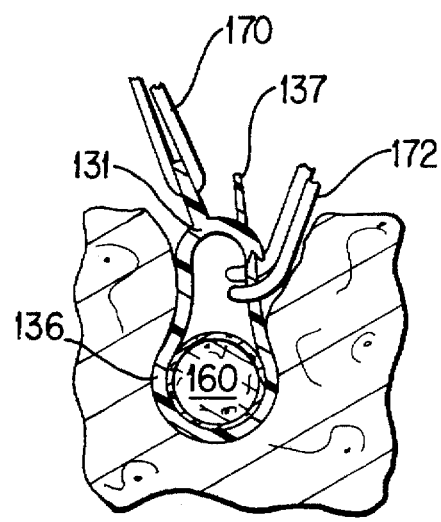
Figure 13C:
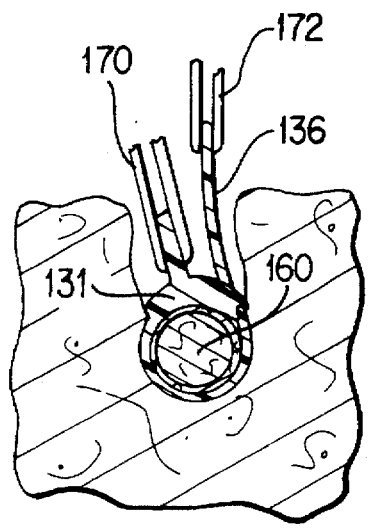
Figure 13D:
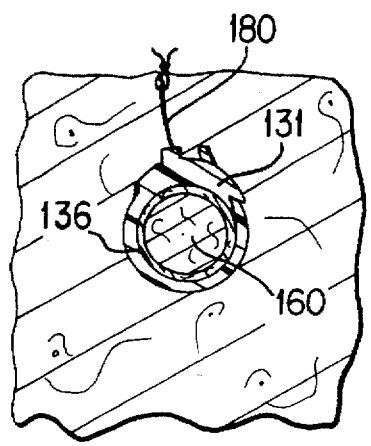

Application of a device to a vessel deep within a tissue 150, as described above, is illustrated in FIGS. 13A-13D. The user first grips the head 131 of the device by grasping the projection 130 with a first pair of forceps (or hemostats or suture clamps) 170. The user can then use a second pair of forceps 172 to slide the strap 136 around a vessel 160 needing repair, as shown in FIG. 13A. The second pair of forceps 172 is then used to insert the tip 137 of the strap 136 into the channel 134 in the head 131, as shown in FIG. 13B. The first pair of forceps 170 can then be used to lower the head 131 to an optimal position over the vessel 160, as shown in FIG. 13C, as the strap 136 is drawn through the head 131 to tighten the device around the vessel 160. Finally, the projection 130 that was used to hold the device, and excess strap 136 material can be clipped off, as shown in FIG. 13D.

The device can be sutured to surrounding tissue to immobilize the device. Alternately, fibrin glue or other means may be used to immobilize the device. It is also possible for adhesive strips to be located on the underside of the head 131, or on the inside of the strap 136 to attach the strap to the vessel 160.

The strap 136 may be manufactured so that it naturally assumes a curved closed position wherein the tip 137 of the strap naturally positions itself near the mouth of the channel 134 in the head 131. This natural curvature will aid in wrapping the strap 136 around the vessel, and in inserting the strap 136 through the channel 134 in the head 131.

Although the device shown in FIGS. 11A-11D includes a strap having a plurality of raised portions 138, the strap 136 and the head 131 may have any sort of design that allows the device to assume different internal diameters, and to apply varying amounts of pressure to a vessel. For instance, the strap 136 may have a plurality of depressions on its outer surface that are engaged by a finger, or pawl, in the channel 134 of the head 131, as shown in FIG. 12.

The strap 136 and the channel 134 may also be smooth walled, but dimensioned to have an interference fit. In this instance, pulling on the end of the strap 136 would cause the strap 136 to stretch, thereby decreasing the thickness of the strap. The decreased thickness of the strap 136 would allow the strap 136 to be pulled through the channel 134 to adjust the internal diameter of the device. The tip 137 of the strap can be made to be thinner than the remainder of the strap 136 to allow the tip 137 to be easily inserted through the channel 134 in the head 131. Once tension is removed from the strap 136, the strap 136 would expand to its original thickness, thereby creating the interference fit.

In addition, the strap 136 and the head 131 may have a release mechanism that allows the strap 136 to be removed from the head 131. For instance, if the strap 136 has the plurality of raised portions, as shown in FIGS. 11A-11D, the portion of the strap 136 protruding above the head 131 may be sliced off with a scalpel or clipped off, thereby removing the raised portions 138 on the strap 136 that prevent the strap 136 from passing back through the channel 134. This would facilitate removal of the strap 136 from the head 131.

If the strap 136 and head 131 utilize a ratcheting or pawl and notch type latching device, the head may be provided with a release mechanism to disengage the pawn from the notches to free the strap.

If the strap 136 and the channel 134 are dimensioned to have an interference fit, the head may be squeezed with forceps or a hemostat to cause the channel 134 to deform and bow outward, thus increasing the thickness of the channel 134 and releasing the strap 136. The head 131 may be provided with projections 145 on the sides of the head 131 adjacent the channel 134 to facilitate grasping and squeezing the head 131 to increase the thickness of the channel 134.

In a preferred embodiment of the device, the strap 136 has only one, or a small number, of raised projections 138. This causes the device to close to only one, or only a few internal diameters, thus preventing the surgeon from inadvertently over-tightening the device. Different sizes of the device could be produced, and the diameter of the device in the closed position may be indicated by a label, or a raised ridge of material, on the projection 130, as shown in FIGS. 11A and 11D. A device having many raised portions 138 would only be necessary where the diameter of the vessel being repaired is unknown or the degree of pressure needed to achieve a seal is unknown.

Shallow ridges 135 may also be formed on the underside of the head 131, and/or on the vessel contacting surface of the strap 136, as shown in FIGS. 11B and 11C. The shallow ridges 135a could be oriented in the circumferential direction of a vessel surrounded by the device provided the ridges are limited to the areas that do not approach the areas on the vessel being sealed so that there is no danger that the ridges will hold an aperture in the vessel open. Some shallow ridges 135b could also be provided on the strap 136. The shallow ridges 135b on the strap could be oriented in the longitudinal axial direction of a vessel surrounded by the device. The shallow ridges 135a, 135b would help to prevent relative movement between the device and the vessel. The ridges 135a, 135b must be shallow enough to prevent unduly narrowing the vessel, and to avoid unnecessary turbulence in the vessel that might lead to intravascular clotting. Alternately, the shape of the inner surface of the head may be varied, or the inner surfaces of the device may be slightly rough to accomplish the same purposes.

Figure 14:
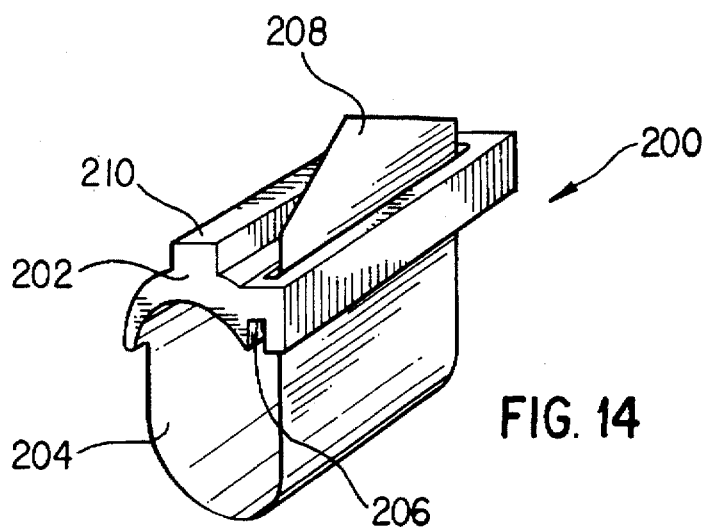
FIG. 14 is a perspective view of a device embodying the present invention.

Another embodiment of the device is shown in FIG. 14. This embodiment has a greater length and is useful in repairing long ruptures or incisions in a vessel, and for correcting an aneurysm. The device 200 includes a head 202 and a strap 204. The strap 204 has a wide tip 208 to facilitate inserting the strap 204 into a channel 206 in the head 202. A raised ridge 210 is provided on the head 202 to facilitate grasping and positioning the device 200.

Figure 15A:
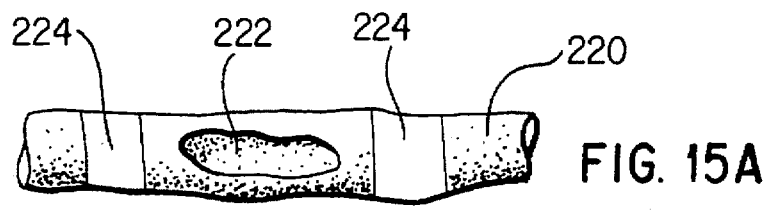
FIGS. 15A and 15B are side views illustrating different methods of repairing a rupture in a vessel.
Figure 15B:
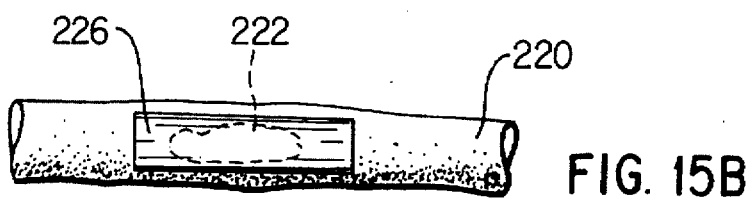

A vessel 220 having a long rupture 222 is shown in FIGS. 15A and 15B. The margins of the rupture 222 are so far apart that it is impossible to join the margins together prior to installing the repair device 200 around the vessel 220.

One method of solving this problem is shown in FIG. 15A. In this method, a pro-coagulant powder or paste is applied to the vessel 220 at regions 224 opposite the rupture 222. Alternately, the pro-coagulant may be applied to the strap 204 of the device 200 at the portions of the strap 204 that will contact regions 224 on the vessel 220. The device 200 is then installed around the vessel 220. The strap 204 of the device 200 will serve to substantially seal the rupture 222, and the pro-coagulant ensures that any escaping blood will clot, further helping to seal the vessel. The pro-coagulant cannot be applied directly to the rupture 222, or to the portions of the strap 204 that contact the rupture 222, because the pro-coagulant might cause intravascular clotting. For this application, the portion of the strap 204 that contacts the rupture 222 is preferably made of a non-thrombogenic material.

A second method of sealing a long rupture 222 in a vessel 220 is illustrated in FIG. 15S. In this method, a strip of non-thrombogenic material 226 is applied to the vessel 220 so that it covers the rupture 222. The strip of non-thrombogenic material 226 acts as an artificial vessel wall. The device 200 is then installed around the vessel 220. When this method is used, a pro-coagulant may be applied to the entire inner surface of the strap 204 of the repair device 200 because the strip of non-thrombogenic material 226 will prevent the pro-coagulant from entering the vessel 220 and causing intravascular clotting.

The device shown in FIG. 14 may also be used to treat an aneurysm as previously described in reference to FIGS. 7A–7C.

Figure 16A:
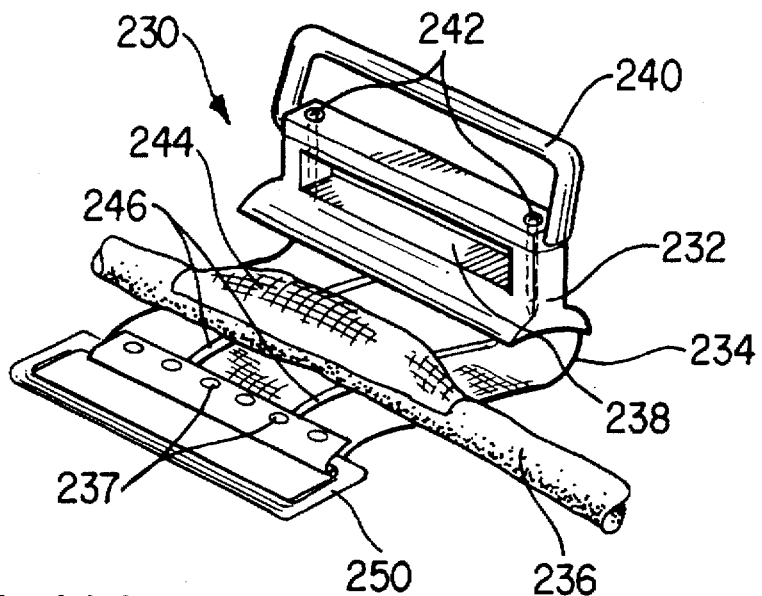
FIGS. 16A–16C show perspective views of a device embodying the invention and illustrate how the device can be used to correct a vascular aneurysm.

A device embodying the invention and particularly well suited to correcting a large aneurysm on a major vessel is shown in FIG. 16A. In this embodiment, the device 230 includes a head 232, a strap 234 and two handles 240, 250. The first handle 240 is attached to the head 232 by one or more screws 242. The second handle 250 is attached to the strap 234 by wrapping the strap 234 around the handle 250 and closing a plurality of snaps 237 provided on the strap 234.

As shown in FIGS. 16A and 16S, the device can be installed around a vessel 236 having an aneurysm by sliding the strap 234 (without the second handle 250) underneath the vessel 236. If minor vessels or other obstructions exist underneath the vessel 236, the strap 234 can be slit 246, to allow the strap 234 to pass around the minor vessels or obstructions. Because the strap 234 is provided with a plurality of snaps 237, the strap 234 can still be secured to the second handle 250, regardless of the presence of slits 246 in the strap 234. Strap 234 may include fibers running from the head 232 to the snaps 237 to facilitate formation of slits in the strap.

Figure 16B:
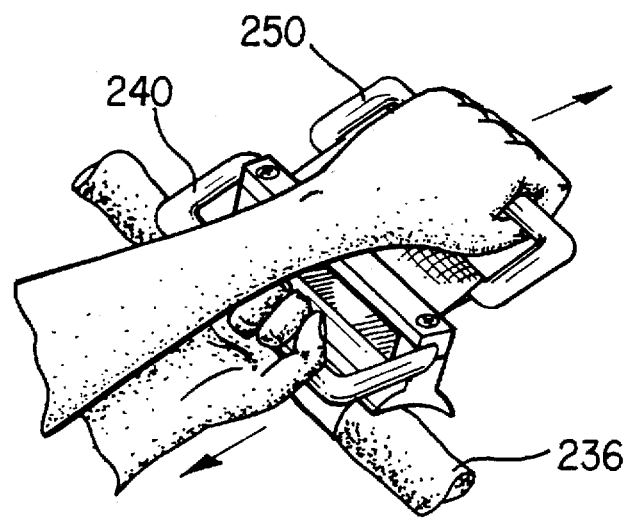
Figure 16C:
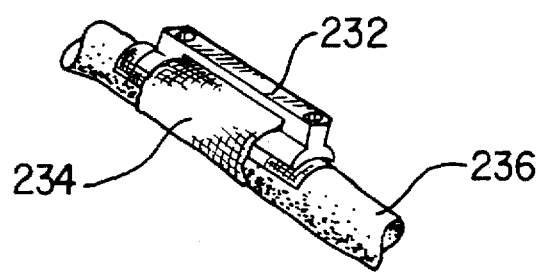

Once the strap has been passed underneath the vessel 236, the strap 234 is attached to the second handle 250, and the strap 234 and handle 250 are passed through an aperture 238 in the head 232. The strap 234 and the head 232 are provided with some sort of latching mechanism as described above in reference to other embodiments of the device. The device 230 is then tightened around the vessel 236 to correct the aneurysm, as shown in FIG. 16B. The first and second handles 240, 250 are removed, and the excess portion of the strap 234 protruding from the head 232 is trimmed off. The result, as shown in FIG. 16C, is that the device 230 is permanently wrapped around the vessel 236 to prevent the aneurysm from reoccurring.

It is also possible to cover the aneurysm on the vessel 236 with a strip of reinforcement material 244 prior to closing and tightening the device 230, as shown in FIG. 16A. The reinforcement material 244 helps to prevent a rupture of the vessel 236 as the device 230 is tightened around the vessel 236. The reinforcement material may have an adhesive on its vessel facing side.

It is also possible to provide a tightening mechanism (not shown) on the device 230, such as a rotatable wheel or shaft, that allows the device to be gradually tightened around the vessel 236. The tightening mechanism may be helpful in controlling the amount of tension placed on the vessel, or the speed at which the device is tightened. Such a tightening device may also help to avoid collision of the handles with body organs, or ease the process to closing the device.

Figure 17:
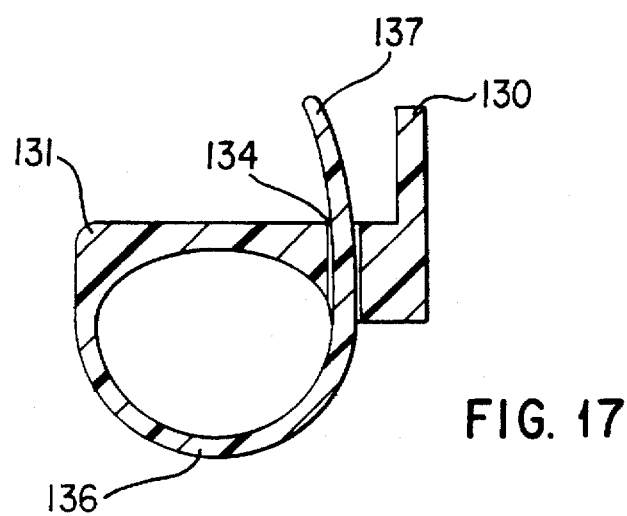
FIG. 17 shows a side sectional view of a device embodying the invention.

FIG. 17 shows another device embodying the invention. In this device a head 131 has a projection 130 located adjacent a channel 134 passing through the head 131. The strap 136 passes through the channel 134 and can be closed with a closure mechanism.

Figure 18A:
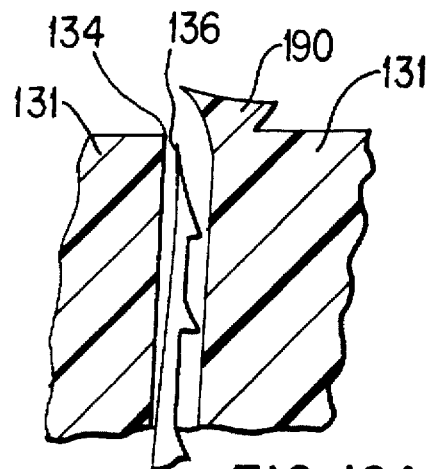
FIGS. 18A–18C are side sectional views of a closure mechanism of a device embodying the invention.
Figure 18B:
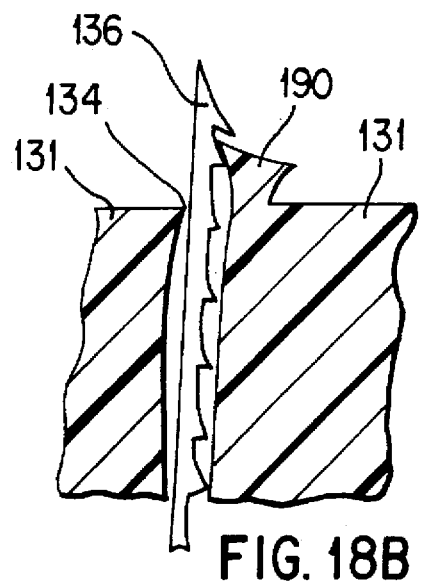
Figure 18C:
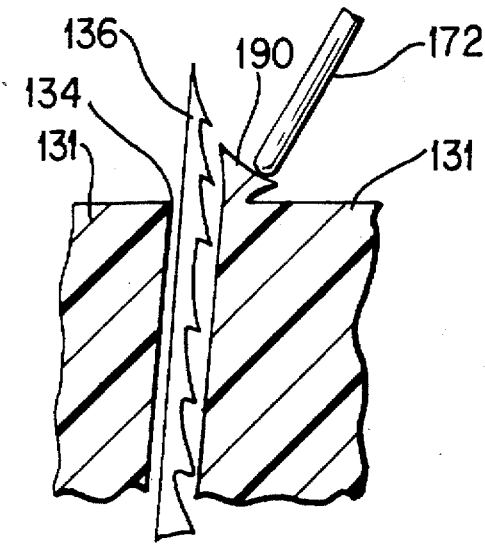

A closure mechanism that can be used on a device embodying the invention is shown in FIGS. 18A–18C. The closure device comprises a flexible pawl 190 on a head 131 of a device embodying the invention. The strap 136 is drawn through a channel 134 in the head until the strap 136 emerges out the top of the head 131. As the strap 136 moves past the pawl 190, the pawl is pushed aside. The pawl 190 engages projections on the strap to prevent the strap from being withdrawn back through the channel 134. If the user of the device wishes to remove or re-position the device, forceps 172 may be used to push down on the pawl 190, to cause the pawl 190 to disengage from the projections on the strap 136. The strap can then be withdrawn from the channel 134.

Figure 19:
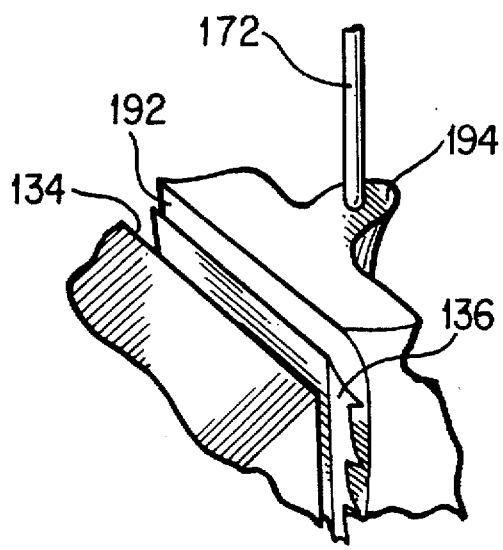
FIG. 19 is a perspective view of a closure and release mechanism of a device having a wide strap.

As shown in FIG. 19, such a closure mechanism can be used on a device having a wide strap. In this embodiment an edge 192 of the channel 134 can be designed to engage projections on a strap passing through the channel 134. The edge 192 may be movable to disengage the strap 136 by pushing on a release tab 194 with forceps 172.

Figure 20:
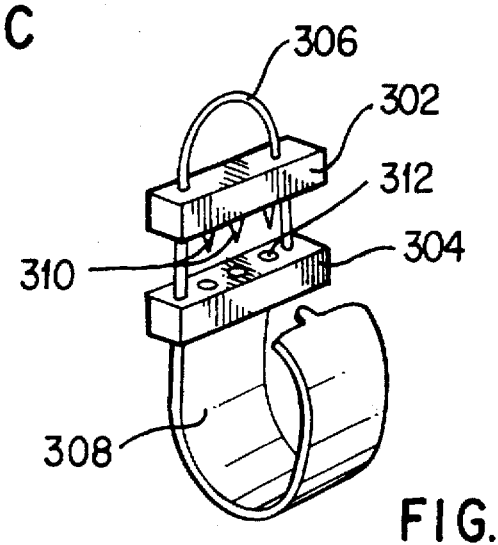
FIG. 20 is a perspective view of a device embodying the invention.

Another device embodying the invention is shown in FIG. 20. The device includes a strap 308 that is insertable through a closure mechanism comprised of cooperating jaws 302, 304. A first jaw 302 includes one or more teeth 310. The second jaw 304 includes apertures 304 that receive corresponding teeth 310 on the first jaw 302. The first jaw is slidable along a loop 306. The strap can be inserted between the jaws, then the first jaw 302 can be slid along the loop 306 until the teeth 310 on the first jaw 302 pierce the strap 308 and enter the apertures 312 on the second jaw 304. This ensures that the strap cannot be loosened. To release the device, the first jaw 302 can be slid along the loop 306, and the strap 308 can be removed from between the jaws.

As will be clear from the foregoing description, many different sizes of the device could be manufactured to allow repair of different sized vessels.

While this invention has been described in conjunction with specific embodiments thereof, it is evident that many alternatives, modifications and variations will be apparent to those skilled in the art. Accordingly, the preferred embodiments of the invention as set forth herein are intended to be illustrative only, and not limiting. Various changes may be made without departing from the spirit and scope of the invention as defined in the following claims.

What is claimed is:

1. A vessel repair device for encircling a vessel, the vessel repair device able to perform at least one of sealing a breach in a wall of the vessel, correcting an aneurysm in the vessel, and reversibly applying pressure to an elongated portion on the exterior of the vessel, the device comprising:

a strap having a width substantially greater that its thickness for surrounding an elongated portion of the exterior of the vessel, the strap having a laterally extending elongated surface for contacting the elongated portion of the vessel, and an exterior surface; and a closure device including a continuous inner wall defining an enclosed aperture that extends therethrough for releasably holding the strap in a closed position around the vessel, wherein the width of the strap is substantially constant along a length extending between a first end adjacent the closure device and a second end and wherein the width of the laterally extending elongated surface of the strap is sufficiently wide and configured for at least one of covering a breach in the wall of the vessel, correcting an aneurysm in the vessel, and reversibly applying pressure to the elongated portion of the exterior of the vessel.

2. The device of claim 1, further comprising a projection located on the extending elongated surface of the strap, the projection having a size and shape such that when the device is closed around a vessel, the projection substantially fills a gap between the extending elongated surface of the strap and an exterior surface of the vessel.

3. The device of claim 1, further comprising at least one positioning member attached to one of the strap and the closure device, the positioning member aiding a user in positioning and closing the device around a vessel.

4. The device of claim 1, further comprising a layer of pro-coagulant material located on the vessel contacting surface of the strap.

5. The device of claim 1, wherein the strap has a first end and a second end, the aperture of the closure device being formed in the first end of the strap, and wherein the closure device further comprises:

an adjustment finder having a first end attached to the second end of the strap; and an adjustment bar that is fixable in the aperture, the adjustment bar being slidably attached to the adjustment finger such that when the adjustment bar is fixed in the aperture, the device is closable at a plurality of positions depending on where the adjustment bar is attached to the adjustment finger.

6. A vessel repair device for encircling a vessel, the vessel repair device able to perform at least one of sealing a breach in a wall of the vessel, correcting an aneurysm in the vessel, and reversibly applying pressure to an elongated portion on the exterior of the vessel, the device comprising:

a strap having a width substantially greater that its thickness for surrounding an elongated portion of the exterior of the vessel, the strap having a laterally extending elongated surface for contacting the elongated portion of the vessel, and an exterior surface; and a closure device for releasably holding the strap in a closed position around the vessel, wherein the width of the strap is substantially constant along a length extending between a first end adjacent the closure device and a second end and wherein the width of the laterally extending elongated surface of the strap is sufficiently wide and configured for at least one of covering a breach in the wall of the vessel, correcting an aneurysm in the vessel, and reversibly applying pressure to the elongated portion of the exterior of the vessel and wherein the strap comprises a first portion and a second portion, and the closure device comprises:

an aperture in the first portion of the strap; and at least one raised portion on the exterior surface of the second portion of the strap, where the second portion of the strap, the at least one raised portion and the aperture are dimensioned such that the second portion of the strap and the at least one raised portion are pullable through the aperture, and such that the device is closable in at least one position due to the physical interference between the aperture and the at least one raised portion.

7. The device of claim 6, wherein the at least one raised portion comprises a plurality of raised portions such that the device is closable in a plurality of positions.

8. The device of claim 6, wherein the aperture comprises walls that are angled with respect to the extending elongated surface of the strap such that when the device is closed around a vessel, substantially no gaps exist between the vessel contacting surface of the strap and an exterior wall of the vessel.

9. A vessel repair device for encircling a vessel, the vessel repair device able to perform at least one of sealing a breach in the vessel, correcting aneurysms in the vessel, and reversibly applying pressure to an elongated portion of the exterior of the vessel, the device comprising:

a head, comprising:

an arcuate surface for contacting the elongated portion of the vessel, and a channel formed therein;

a strap attached to the head and having an extending elongated surface for contacting the elongated portion of the vessel, the strap having a width substantially greater than its thickness and an exterior surface, the strap being passable around a vessel and through the channel in the head; and a closure device for releasably holding the vessel repair device closed around a vessel;

wherein the width of the strap is substantially constant along a length extending between a first end attached to the head and a second end and wherein the width of the extending elongated surface of the strap is sufficiently wide and configured for at least one of covering the elongated portion of the vessel to seal a breach in the vessel, correcting aneurysms in the vessel, and reversibly applying pressure to the elongated portion of the exterior of the vessel.

10. The device of claim 9, wherein the channel and the strap are dimensioned so that the device is closable in at least one position due to friction between the channel and the strap.

11. The device of claim 9, further comprising at least one raised portion on the strap, the device being closable in at least one position due to physical interference between the channel and the at least one raised portion.

12. The device of claim 11, wherein the head is deformable to increase a dimension of the channel, the increase in the dimension of the channel eliminating physical interference between the channel and the at least one raised portion so that the strap is withdrawable from the channel.

13. The device of claim 9, wherein the head further comprises a projection that is graspable by a user to aid positioning and closure of the device.

14. The device of claim 9, further comprising at least one ridge on one of the arcuate extending contacting surface and the extending elongated surface of the strap, friction between the ridge and the exterior surface of a vessel preventing movement of the device relative to the vessel when the device is closed around the vessel.

15. The device of claim 9, further comprising:
a first handle, attachable to the head; and
a second handle, attachable to the scrap.

16. The device of claim 9, wherein the closure device comprises:
at least one recess on the strap; and
a pawl member attached to the head and extending into the channel, wherein the pawl member is engagable in the at least one recess when the strap is inserted into the channel to prevent withdrawal of the strap from the channel.

17. An apparatus for repairing a breach or an aneurysm in a vessel wall or reversibly applying pressure to an elongated portion on the exterior of the vessel wall, comprising:
strap means for surrounding a vessel having a breach or an aneurysm so that the strap means covers the breach or aneurysm; and
means for reversibly applying pressure to the exterior of the elongated portion of the vessel with the strap means to prevent leakage of fluid from the breach or reoccurrence of the aneurysm, and to prevent relative movement between the vessel and the strap means, said means for reversibly applying pressure comprising a continuous inner wall of the strap means which defines an enclosed aperture for releasably holding an end portion of the strap means therein;
wherein a width of the strap means is substantially constant along a length extending between first and second ends wherein a surface of the strap means has a width that is substantially greater than its thickness and is sufficiently wide and configured for at least one of covering the elongated portion of the vessel to seal a breach in the vessel, correcting aneurysms in the vessel, and reversibly applying pressure to the elongated portion of the exterior of the vessel.

18. A vessel repair device, comprising:
a strap for surrounding the exterior of a vessel, the strap having a surface for contacting a vessel and an exterior surface;
a closure device including a continuous inner wall defining an enclosed aperture that extends therethrough for releasably holding the strap in a closed position around the vessel; and
at least one positioning member attached to one of the strap and the closure device and extending in a direction away from the surface for contacting a vessel, the at least one positioning member being configured so that a user can grasp the at least one positioning member to aid in positioning and closing the device around a vessel.

19. A vessel repair device, comprising:
a head, comprising:
an arcuate surface for contacting a vessel, and
a channel formed therein;
a strap attached to the head and having a surface for contacting a vessel and an exterior surface, the strap being passable around a vessel and through the channel in the head;
a closure device for holding the device closed around a vessel; and
at least one positioning member attached to one of the strap and the closure device and extending in a direction away from the surface for contacting a vessel, the at least one positioning member being configured so that a user can grasp the at least one positioning member to aid in positioning and closing the device around a vessel.

20. An apparatus for repairing a breach or an aneurysm in a vessel wall, comprising:
strap means for surrounding a vessel having a breach or an aneurysm so that the strap means covers the breach or aneurysm; and
means for reversibly applying pressure to the exterior of the vessel with the strap means to prevent leakage of fluid from the breach or reoccurrence of the aneurysm, and to prevent relative movement between the vessel and the strap means, said means for reversibly applying pressure comprising a continuous inner wall of the strap means which defines an enclosed aperture for releasably holding an end portion of the strap means therein; and
positioning means for positioning and closing the apparatus around a vessel, the positioning means extending away from the strap means and being configured so that a user can grasp the positioning means to position and close the device around a vessel.

21. A method of encircling a vessel to perform at least one of sealing a breach in a wall of the vessel, correcting an aneurysm in the vessel, and reversibly applying pressure to an elongated portion on the exterior of the vessel, the method comprising:
surrounding the elongated portion of the exterior of the vessel with a strap having a width substantially greater that its thickness, a laterally extending elongated surface for contacting the elongated portion of the vessel, and an exterior surface; and
releasably holding the strap in a closed position around the vessel by means of a closure device having an aperture for releasably holding an end portion of the strap therein,
wherein the width of the strap is substantially constant along a length extending between a first end adjacent the closure device and a second end and wherein the width of the laterally extending elongated surface of the strap is sufficiently wide and configured for at least one of covering a breach in the wall of the vessel, correcting an aneurysm in the vessel, and reversibly applying pressure to the elongated portion of the exterior of the vessel.

22. The method of claim 21, further comprising the step of fixing the strap around the vessel to keep the breach or aneurysm from reoccurring.

23. The method of claim 21, further comprising the step of covering the breach or aneurysm with a layer of reinforcing material before surrounding the vessel with the strap.

* * * * *